United States Patent [19]

Shibasaki et al.

[11] Patent Number: 4,681,951
[45] Date of Patent: Jul. 21, 1987

[54] BICYCLO(3.3.0)OCTENE DERIVATIVES

[75] Inventors: Masakatsu Shibasaki; Toshiaki Mase, both of Tokyo; Mikiko Sodeoka; Yuji Ogawa, both of Sagamihara, all of Japan

[73] Assignee: Sagami Chemical Research Center, Tokyo, Japan

[21] Appl. No.: 641,587

[22] Filed: Aug. 17, 1984

[30] Foreign Application Priority Data

Dec. 27, 1983 [JP] Japan .................................. 58-244695
Feb. 10, 1984 [JP] Japan .................................. 59-22010
Mar. 28, 1984 [JP] Japan .................................. 59-58458

[51] Int. Cl.$^4$ ..................... C07D 309/10; C07C 47/40
[52] U.S. Cl. ..................................... 549/214; 549/417; 549/420; 556/436; 556/437; 560/107; 560/256; 568/445
[58] Field of Search ................. 568/445; 560/107, 256; 549/417, 420, 214; 556/436, 437

[56] References Cited

U.S. PATENT DOCUMENTS 4,225,507  9/1980  Sih ................................... 568/445 X
4,292,432  9/1981  Ono et al. ......................... 568/445 X

Primary Examiner—Dolph H. Torrence

Attorney, Agent, or Firm—Schwartz, Jeffery, Schwaab, Mack, Blumenthal & Evans

[57] ABSTRACT

There are disclosed bicyclo[3.3.0]octene derivatives having the following formula:

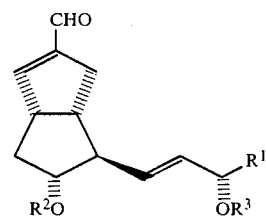

wherein
$R^1$ is a straight, branched or cyclic alkyl group or alkenyl group each having 5 to 10 carbon atoms; and
$R^2$ and $R^3$ are each separately a hydrogen atom or a protective group of a hydroxy group, and process for producing the same. These compounds and the process for producing them are available for producing a 9(0)-methano-Δ6(9α)-PGI$_1$.

1 Claim, No Drawings

BICYCLO(3.3.0)OCTENE DERIVATIVES

BACKGROUND OF THE INVENTION

This invention relates to a bicyclo[3.3.0]octene derivative and a process for producing the same.

9(0)-methano-$\Delta^{6(9\alpha)}$-PGI$_1$ has a potent platelet aggregation inhibiting action. For example, its action is comparable to chemically unstable PGI$_2$, when human platelet is employed, and it is a compound which can be utilized as a therapeutic or preventive for various diseases of circulatory organs (see the test examples shown below).

In the prior art, as the process for producing 9(0)-methano-$\Delta^{6(9\alpha)}$-PGI$_1$, there have been known (a) the process in which it is produced through the 14 steps using PGE$_2$ as the starting material [Preliminary Text for Lectures in 103rd Annual Meeting in Pharmaceutical Society of Japan, p. 156, (1983)] and (b) the process in which it is produced from 1,3-cyclooctadiene through 19 steps [Preliminary Text for Lectures in 103rd Annual Meeting in Pharmaceutical Society of Japan, p. 157, (1983)]. The former process has the drawback that the starting material is expensive, while the latter process that the desired product is formed as a racemic mixture. Further, both processes (a) and (b) are also disadvantageously very low in the overall yield.

SUMMARY OF THE INVENTION

The present inventors have studied extensively to produce 9(0)-methano-$\Delta^{6(9\alpha)}$-PGI$_1$ from a cheap starting material at good yield and with optical activity as well as steric configuration specificity, and consequently found that the compound of the present invention and the process for producing the same can be an important intermediate and a process for achieving the object to accomplish the present invention.

This invention concerns a compound of the formula:

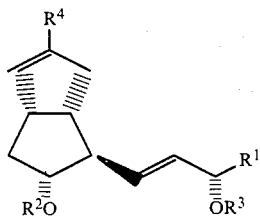

[I]

wherein
R$^1$: a straight, branched or cyclic alkyl group or alkenyl group each having 5 to 10 carbon atoms;
R$^2$ and R$^3$: each represent a hydrogen atom or a protective group of a hydroxy group; and
R$^4$: —CHO, —CH=CH—(CH$_2$)$_2$—COOR$^5$ or —CH$_2$R$^6$; where
R$^5$: a hydrogen atom or an alkyl group; and
R$^6$: a hydroxy group, an acetyloxy group or a butenyl group,
and a process for producing the same.

DESCRIPTION OF THE PREFERRED EMBODIMENTS

The bicyclo[3.3.0]octene derivative represented by the above formula [I] of this invention can be led to 9(0)- methano-$\Delta^{6(9\alpha)}$-PGI$_1$ and derivatives thereof as follows: Namely, among the above bicyclo[3.3.0]octene derivatives, bicyclo[3.3.0]octenylaldehyde derivatives which are R$^4$ being —CHO can be led to 9(0)-methano-$\Delta^{6(9\alpha)}$-PGI$_1$ by subjecting them to elongation reaction of $\alpha$-chain by using Wittig reagent which is prepared by 3-carboxypropyltriphenylphosphonium bromide and a base, subjecting a hydroxy group to deprotection reaction, then subjecting a double bond selectively to reduction and thereafter subjecting an ester to hydrolysis; (4'-alkoxycarbonyl-1'-alkenyl)-cis-bicyclo[3.3.0]octene derivatives which are R$^4$ being —CH=CH—(CH$_2$)$_2$—COOR$^6$ can be led the same by subjecting them to elongation reaction of $\alpha$-chain, subjecting a hydroxy group to deprotection reaction and thereafter subjecting an ester to hydrolysis; and bicyclo[3.3.0]octene derivatives which have R$^4$ being —CH$_2$R$^5$ can be led the same by subjecting them to hydration reaction, then subjecting a hydroxy group to deprotection reaction, and thereafter subjecting to oxdation reaction (see the following Reference examples).

The protective group of hydroxy group in this invention may include, for R$^2$, a tetrahydropyranyl group, a methoxymethyl group, a 4-methoxytetrahydropyranyl group, a 1-ethoxyethyl group, a 1-methyl-1-methoxyethyl group, a t-butyldimethylsilyl group, a diphenyl-t-butylsilyl group, a benzoyl group, an acetyl group, etc. and, for R$^3$, a t-butyldimethylsilyl group, a benzoyl group, an acetyl group, a tetrahydropyranyl group, a methoxymethyl group, a 4-methoxytetrahydropyranyl group, a 1-ethoxyethyl group, a 1-methyl-1-methoxyethyl group, a diphenyl-t-butylsilyl group, etc.

The bicyclo[3.3.0]octene derivative represented by the above formula [I] can be produced according to the reaction schemes as shown below.

In the compounds of the present invention, (4'-alkoxycarbonyl-1'-alkenyl)-cis-bicyclo[3.3.0]octene derivatives [I-c] can be prepared following the reaction schemes shown below:

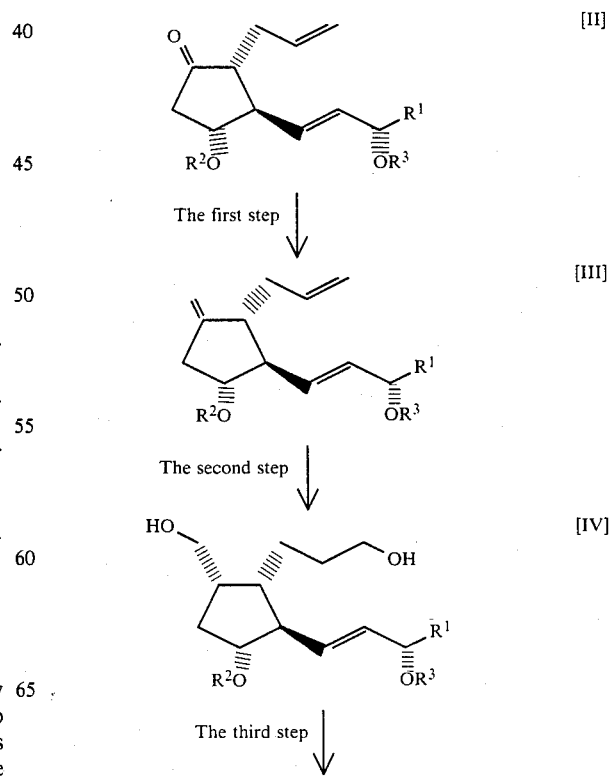

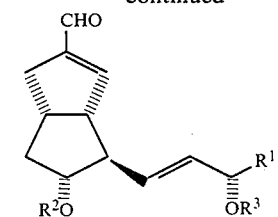

The fourth step ↓

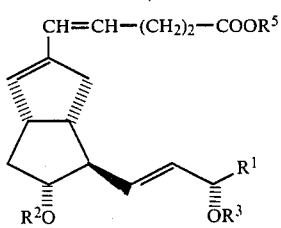

The fifth step ↓

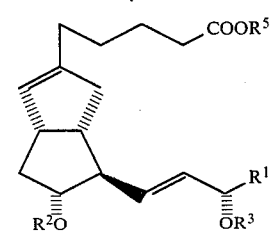

wherein R¹, R², R³ and R⁵ are the same as defined above.

[The first step]

This step produces an allyl cyclopentylidene derivative represented by the formula [III] by methylenation of an allyl cyclopentanone derivative represented by the above formula [II].

The allyl cyclopentanone derivative which is employed as the starting material of this step is produced by reacting a cyclopentenone represented by the formula [V]:

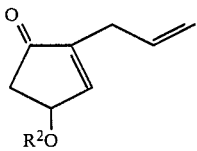

wherein R² represents a protective group of a hydroxy group, with an organic copper compound represented by the formula [VI]:

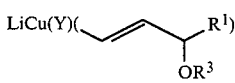

wherein R¹ is the same meaning as defined above; R³ represents a protective group of a hydroxy group; and Y represents a group of

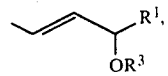

phenylthio group or a 1-pentynyl group (see Japanese Provisional Patent Publication No. 171965/1982).

Examples of the thus obtained compounds may be {2(R)-allyl-3(R)-[3'(S)-t-butyldimethylsilyloxy-1'-transoctenyl]-4(R)-t-butyldimethylsilyloxy-1-cyclopentanone}, {2(R)-allyl-3(R)-[3'(S)-t-butyldimethylsilyloxy-3'-cyclopentyl-1'-trans-propenyl]-4(R)-t-butyldimethylsilyloxy-1-cyclopentanone}, {2(R)-allyl-3(R)-[3'(S)-t-butyldimethylsilyloxy-4'-methyl-1'-transoctenyl]-4(R)-t-butyldimethylsilyloxy-1-cyclopentanone}, {2(R)-allyl-3(R)-[3'(S)-tetrahydropyranyloxy-1'-trans-octenyl]-4(R)-tetrahydropyranyloxy-1-cyclopentanone}, {2(R)-allyl-3(R)-[3'(S)-tetrahydropyranyloxy-3'-cyclopentyl-1'-trans-propenyl]-4(R)-tetrahydropyranyloxy-1-cyclopentanone}, {2(R)-allyl-3(R)-[3'(S)-tetrahydropyranyloxy-4'-methyl-1'-transoctenyl]-4(R)-tetrahydropyranyloxy-1-cyclopentanone}, {2(R)-allyl-3(R)-[3'(S)-(1'-ethoxyethyloxy)-1'-trans-octenyl]-4(R)-(1'-ethyoxyethyloxy)-1-cyclopentanone}, {2(R)-allyl-3(R)-[3'(S)-(1'-ethoxyethyloxy)-3'-cyclopentyl-1'-trans-propenyl]-4(R)-(1'-ethoxyethyloxy)-1-cyclopentanone}, {2(R)-allyl-3(R)-[3'(S)-(1'-ethoxyethyloxy)-4'-methyl-1'-trans-octenyl]-4(R)-(1'-ethoxyethyloxy)-1-cyclo-pentanone} and the like.

The methylenation in this step may be carried out by use of a mixed reagent of methylene bromide-titanium tetrachloride-zinc [L. Lombardo, Tetrahedron Lett., 23, 4293 (1982)] or Johnson reagent [C. R. Johnson, J. R. Shanklin, R. A. Kirchoff, J. Am. Chem. Soc., 95, 6462 (1973)].

The reaction should desirably be carried out in a solvent, for example, a solvent mixture such as a halogenic solvent (e.g. methylene chloride)—an ether solvent (e.g. tetrahydrofuran) in the case of using the former reagent, while an ether solvent in the case of the latter reagent.

The reaction can proceed smoothly at −80° C. to 60° C., but room temperature is preferred because the reaction can be carried out without heating or cooling.

[The second step]

This step produces a hydroxymethyl cyclopentane derivative represented by the above formula [IV] by hydration of an allyl cyclopentylidene derivative represented by the above formula [III].

The hydration reaction in this step is conducted out by hydroboration and oxidation. In carrying out hydroboration, there may be employed a hydroborating reagent such as 9-BBN (9-borabicyclo[3.3.1]nonane), disiamylborane, thexylborane, etc. The amount of the hydroborating agent used may be generally 1 to 3 equivalent.

The reaction is desired to be carried out in a solvent, preferably an ether type solvent such as tetrahydrofuran, diglyme, diethylether, etc.

The reaction proceeds smoothly at −25° C. to room temperature.

Further, this step carries out oxidation of the product subsequent to the hydroboration without isolation thereof. The oxidation may be carried out by use of an oxidizing agent such as an alkaline hydrogen peroxide, an amine oxide, oxygen, peracid, etc. The amount of the oxidizing agent employed may be 5 to 15 equivalents.

The reaction proceeds smoothly at room temperature to 60° C.

In this step, the compound formed by hydroboration with the use of, for example, 9-BBN may be estimated to have a formula as shown below:

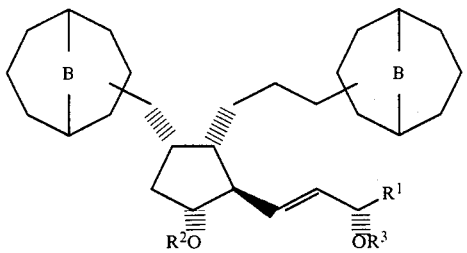

[The third step]

This step produces a bicyclo[3.3.0]octenylaldehyde derivative represented by the above formula [I-b] by oxidation and dehydration of the hydroxymethyl cyclopentane derivative represented by the above formula [IV] obtained by the above second step.

In carrying out oxidation, it is possible to use a dimethylsulfoxide-oxalyl chloride, dimethylsulfoxidepyridine complex of sulfur trioxide, etc. The amount of the oxidizing agent employed may be generally 1 to 5 equivalents.

The reaction is desired to be carried out in a solvent, for example, a halogenated hydrocarbon such as methylene chloride.

The reaction can proceed smoothly at a temperature, which may differ depending on the oxidizing agent employed, but generally at $-70°$ C. to room temperature.

For obtaining the oxidized product in this step, a tertiary amine such as triethylamine, diisopropylethylamine, etc. is added into the reaction product and treatment is carried out at $-70°$ C. to room temperature.

Further, this step carries out dehydration of the obtained product subsequent to the oxidation without isolation thereof.

Dehydration is required to be carried out in the presence of an acidic catalyst. As the acidic catalyst, an acid-ammonium salt is available. An acid-ammonium salt can be formed from an acid and an amine. The acid available may be exemplified by trifluoroacetic acid, toluenesulfonic acid, camphorsulonic acid, acetic acid, etc. The amine available may be exemplified by dibenzylamine, diethylamine, dimethylamine, diisopropylamine, piperidine, pyrrolidine, piperazine, etc. These acids and amines may appropriately be selected and combined to be provided for use. Above all, the catalyst comprising a combination of trifluoroacetic acid and dibenzylamine is preferred on account of good yield of the desired product. The amount of the catalyst employed may be about 0.2 equivalent, but it is preferred to employ about one equivalent in order to proceed rapidly the reaction.

The reaction is desired to be carried out in a solvent, for example, an aromatic hydrocarbon such as benzene, toluene, xylene, etc.

The reaction temperature may be selected within the range from room temperature to 100° C., but preferably within the range from 50° C. to 70° C. in order to carry out the reaction smoothly.

[The fourth step]

This step produces a (4'-alkoxycarbonyl-1'-alkenyl)-cis-bicyclo[3.3.0]octene derivative represented by the above formula [I-c] by reacting the bicyclo[3.3.0]octenylaldehyde derivative represented by the above formula [I-b] obtained by the above third step with 3-carboxypropyl triphenyl phosphonium halide represented by the formula:

$$(R^7)_3P^\oplus-(CH_2)_3-COOH \quad X^\ominus$$

wherein $R^7$ is an alkyl group or an aryl group, and X is a halogen atom, in the presence of a base.

This step is required to be carried out in the presence of a base. The base may include potassium t-butoxide, butyl lithium, sodium salt of dimethylsulfoxide, etc. For carrying out the reaction with good efficiency, it is preferred to employ potassium t-butoxide. The amount of the base employed may be generally 1 to 1.2 equivalent based on the above 3-carboxypropyl triphenyl phosphonium halide which is employed as one of the starting material. Preferable example of the 3-carboxypropyl triphenyl phosphonium halide is 3-carboxypropyl triphenyl phosphonium bromide.

The reaction may be carried out preferably in an ether solvent such as tetrahydrofuran, dimethoxyethane, diethyl ether, etc. The solvent is not particularly limited, provided that it does not interfere with the reaction.

The reaction temperature may be selected within the range from 0° C. to 50° C., at which the reaction can proceed smoothly.

The compound obtained in this step is formed generally as a free carboxylic acid, but it can be isolated as an ester by use of the condition of diazomethane or alkyl halide-diazabicycloundecene-acetonitrile for the reactions in the subsequent step et seq. Conversion to ester may be conducted according to the method easily done by those skilled in the art.

[The fifth step]

This step produces a bicyclo[3.3.0]octene derivative represented by the above formula [I-a] in which only the disubstituted olefin of α-chain is selectively reduced by catalytic reduction of the (4'-alkoxycarbonyl-1'-alkenyl)-cis-bicyclo[3.3.0]octene derivative represented by the formula [I-c] obtained in the above fourth step.

The available catalysts include palladium catalysts such as palladium-carbon, palladium black, etc., Wilkinson catalysts, platinum, nickel, etc. For carring out the reaction with good efficiency, it is preferred to employ Wilkinson catalyst. The catalyst may be sufficiently employed in the so-called catalytic amount.

In practicing this step, hydrogen may be allowed to react with the compound under normal pressure or under pressurization.

The reaction may be carried out preferably in a solvent, for example, an alcohol solvent such as methanol, ethanol, etc. or an ester solvent such as ethyl acetate, etc.

The reaction can proceed smoothly at a temperature selected within the range from $-25°$ C. to 60° C.

The (4'-alkoxycarbonyl-1'-alkenyl)-cis-bicyclo[3.3.-0]octene derivative of this invention has a asymmetric carbon atom in the molecule, and the present invention includes compounds of a R-configuration, S-configuration and a mixture of a volumtary ratio thereof with regard to the asymmetric carbon atom.

Further, in the above formula [I], the bicyclo[3.3.-0]octene derivatives in which $R^4$ being —$CH_2R^6$ represented by the formula [I-f] can be produced by subjecting bicyclo[3.3.0]octenyl aldehyde derivative represented by the above formula [I-b] to the reaction step as mentioned below:

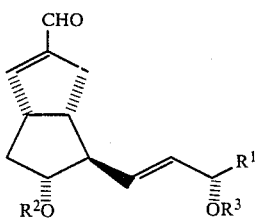
[I-b]

The first step ↓

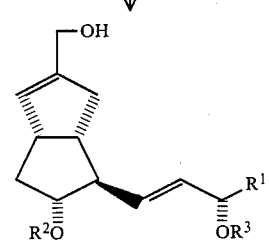
[I-d]

The second step ↓

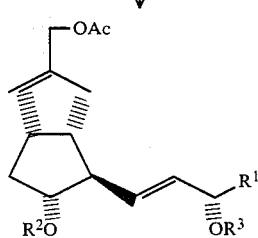
[I-e]

The third step ↓

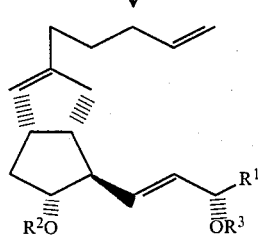
[I-f]

[The first step]

This step produces a bicyclo[3.3.0]octenyl methyl alcohol derivatice represented by the above formula [I-d] by reduction of the bicyclo[3.3.0]octenylaldehyde derivative represented by the above formula [I-b].

In the bicyclo[3.3.0]octnylaldehyde derivatives, the compounds in which $R^1$ are straight or branched alkyl or alkenyl group are prepared according to the method as described in Preliminary text for lectures in 104th annual meeting in Pharmaceutical Society of Japan (1984), p. 282, and the compound in which $R^1$ are cylcic alkyl or alkenyl are prepared according to the same method as mentioned above.

Reduction is required to be carried out in the presence of a reducing agent. As the reducing agent, diisobutylaluminum hydride, sodium borohydride, lithium aluminumhydride and the like are available. The amount of the reducing agent employed may be about one equivalent or slightly excess amount based on the bicyclo[3.3.0]octenylaldehyde derivative represented by the above formula [I-b].

The reaction should desirably be conducted in a solvent, for example, an alcohol solvent such as methanol, ethanol, etc., an ether solvent such as diethyl ether, tetrahydrofuran, etc., an aromatic solvent such as benzene, toluene, etc., and a halogenic solvent such as methylene chloride, chloroform, etc. The solvent may optionally be selected due to the reducing agent to be used. The reaction can proceed smoothly at $-100°$ to $50°$ C.

[The second step]

This step produces a bicyclo[3.3.0]octenylmethylacetate derivative represented by the above formula [I-e] by acetylation of the bicyclo[3.3.0]octenylmethyl alcohol derivative represented by the above formula [I-d] obtained in the above first step.

In carrying out acetylation, it is possible to use an acetic anhydride which is generally employed this type of reaction.

Further, in carrying out this step, it is possible to employ a catalyst such as pyridine, 4-dimethylaminopyridine, etc.

The reaction should desirably be conducted in a solvent, for example, an aromatic solvent such as benzene, toluene, etc., an ether solvent such as diethyl ether, tetrahydrofuran, etc., and a halogenic solvent such as methylene chloride, etc.

The reaction can proceed smoothly at $-25°$ to $100°$ C.

[The third step]

This step produces a pentenylbicyclo[3.3.0]octene derivative represented by the above formula [I-f] by reacting the bicyclo[3.3.0]octenylmethyl acetate derivative represented by the above formula [I-e] obtained in the above second step with lithium dialkylcuprate.

The lithium dialkylcuprate is a compound which is easily prepared by reacting copper (I) iodide with 3-butenyl lithium (as for the preparative method thereof, see R. F. Cunico, Y. K. Han, J. Organomet. Chem., 174, 247 (1977)).

In carrying out this step, an ether solvent such as diethyl ether, tetrahydrofuran, dimethoxyethane, etc. may desirably be employed.

The reaction can proceed smoothly at $-100°$ to $50°$ C.

The present invention is described in more detail by referring to the following Reference examples and Examples.

REFERENCE EXAMPLE 1

To a solution of {2(R)-allyl-3(R)-[3'(S)-t-butyldimethylsilyloxy-1'-trans-octenyl]-4(R)-t-butyldimethylsilyloxy-1-cyclopentanone} (707 mg, 1.44 mmol) dissolved in methylene chloride (7 ml) was added zinc-titanium chloride-methylene bromide reagent (Zn-TiCl$_4$-CH$_2$Br$_2$/THF, 7.48 ml, about 1.3 equivalents) at room temperature. The mixture was stirred at the same condition for 30 minutes so that the starting materials were all reacted. Subsequently, the mixture was poured into the two layer system solution comprising ether-saturated aqueous sodium hydrogencarbonate solution so as to stop the reation. Then, an ether layer was separated from the mixture, and an aqueous layer was extracted with ether. The combined ether layers were washed with a saturated aqueous ammonium chloride solution and saturated saline solution, and dried with anhydrous magnesium sulfate. Evaporation of the solvent, followed by purification through silica gel column chromatography to obtain {2(R)-allyl-3(R)-[3'(S)-t-butyldimethylsilyloxy-1'-trans-octenyl]-4(R)-t-butyldimethylsilyloxy-1-cyclopentylidene} (652 mg, Yield: 88%) as substantially colorless oily products.

IR (neat): 3080, 2930, 2850, 1650, 1460, 1360, 1250 cm$^{-1}$.

NMR δ (CDCl$_3$): 5.70 (m, 1H), 5.41 (m, 2H), 4.75–5.10 (m, 4H), 4.02 (m, 1H), 3.76 (m, 1H), 2.00–2.70 (m, 6H), 1.40 (m, 8H), 0.88 (s, 21H), 0.02 (s, 12H).

Mass m/z (%): 435 (M$^+$-57), 421, 393, 323, 303, 289, 229, 147, 75, 73.

REFERENCE EXAMPLE 2

To {2(R)-allyl-3(R)-[3'(S)-t-butyldimethylsilyloxy-1'-trans-octenyl]-4(R)-t-butyldimethylsilyloxy-1-cyclopentylidene} (700 mg, 1.42 mmol) was added a THF solution (7.10 mmol, 14.2 ml) of 9-borabicyclo[3.3.1]nonane (9-BBN) at room temperature, and the mixture was stirred for 3 hours. Then, to the reaction system were gradually added dropwise a 6 N-NaOH aqueous solution (6.9 ml) and a 30% H$_2$O$_2$ aqueous solution (5.8 ml) at room temperature, and the mixture was stirred at 60° C. for 2 hours. The mixture was extracted with ether, and the separated ether layer was washed with an aqueous sodium thiosulfate solution and water. After dryness with anhydrous magnesium sulfate, followed by evaporation of the solvent and purification through silica gel column chromatography to obtain {1(S)-hydroxymethyl-2(S)-(3'-hydroxypropyl)-3(S)-[3'(S)-t-butyldimethylsilyloxy-1'-trans-octenyl]-4(R)-t-butyldimethylsilyloxy-cyclopentane} (502 mg, Yield: 67%) as colorless oily products.

IR (neat): 3350, 2930, 2850, 1460, 1360, 1250 cm$^{-1}$.

NMR δ (CDCl$_3$): 5.38 (m, 2H), 3.96 (m, 2H), 3.59 (m, 4H), 2.83 (m, 1H), 2.16 (m, 3H), 1.10–1.80 (m, 15H), 0.87 (s, 21H), 0.04 (s, 12H).

Mass m/z (%): 471 (M$^+$-57), 453, 396, 379, 339, 325, 321, 247, 229, 75, 73.

EXAMPLE 1

To a methylene chloride solution (5 ml) of oxalyl chloride (0.46 ml, 5.40 mmol) was added dropwise a methylene chloride solution (4 ml) of DMSO (0.83 ml, 11.7 mmol) at −78° C. for 5 minutes, and the mixture was stirred at the same condition for 15 minutes. To the thus prepared mixture was added dropwise a methylene chloride solution (3 ml) of {1(S)-hydroxymethyl-2(S)-(3'-hydroxypropyl)-3(S)-[3'(S)-t-butyldimethylsilyloxy-1'-trans-octenyl]-4(R)-t-butyldimethylsilyloxycyclopentane} (475 mg, 0.900 mmol), and the mixture was further stirred at −78° C. for 15 minutes. Under the same condition, triethylamine (2.50 ml, 18.0 mmol) was added thereto, then a cooling bath was removed and the mixture was stirred for 15 minutes. Methylene chloride was distilled out under reduced pressure and to the resultant residue were added benzene (8 ml) and trifluoroacetic acid salt of dibenzylamine (220 mg, 0.900 mmol) and the mixture was stirred at 70° C. for 4 hours. The mixture was diluted with ether, washed successively with an aqueous ammonium chloride solution, a saturated aqueous sodium hydrogencarbonate solution and a saturated saline solution and dried with anhydrous magnesium sulfate. After evaporation of the solvent, the residue was purifired through silica gel column chromatography to obtain {3-formyl-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (441 mg, Yield: 97%) as substantially colorless oily product.

IR (neat): 2950, 2850, 1680, 1460, 1360, 1250 cm$^{-1}$.

NMR δ (CDCl$_3$): 9.82 (s, 1H), 6.73 (bs, 1H), 5.48 (m, 2H), 4.08 (m, 1H), 3.76 (m, 1H), 3.24 (m, 1H), 1.10–2.80 (m, 14H), 0.87, 0.90 (2s, 21H), 0.03 (s, 12H).

Mass m/z (%): 449 (M$^+$-57), 435, 359, 339, 317, 303, 202, 73.

EXAMPLE 2

{3-formyl-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (18.9 mg, 0.0374 mmol) was mixed in a mixed solvent of acetic acid-water-tetrahydrofuran (3:1:1) (0.2 ml) and the mixture was stirred at 45° C. for 3 hours. After evaporation of the solvent under reduced pressure, to the residue was added a saturated aqueous sodium hydrogencarbonate solution and extracted with ethyl acetate. The separated organic layer was washed with a saturated saline solution and dried with anhydrous magnesium sulfate. Evaporation of the solvent, followed by purification through silica gel column chromatography to obtain {3-formyl-6(S)-[3'(S)-hydroxy-1'-trans-octenyl]-7(R)-hydroxy-(1S,5S)-cis-bicyclo[3.3.0]oct-2-ene} (8.3 mg, Yield: 80%) as substantially colorless oily product.

IR (neat): 3400, 2950, 2850, 1680 cm$^{-1}$.

NMR δ (CDCl$_3$): 9.82 (s, 1H), 6.73 (bs, 1H), 5.45 (m, 2H), 4.10 (m, 1H), 3.80 (m, 1H), 3.24 (m, 1H).

Mass m/z (%): 278 (M$^+$), 260 (M$^+$-H$_2$O).

REFERENCE EXAMPLE 3

In the method as described in Reference examples 1 and 2, the same procedures were carried out as in Reference examples 1 and 2 except that {2(R)-allyl-3(R)-[3'(S)-tetrahydropyranyloxy-1'-trans-octenyl]-4(R)-tetrahydropyranyloxy-1-cyclopentanone} (434 mg, 1 mmol) was employed as the starting material to obtain {1(S)-hydroxy-methyl-2(S)-(3'-hydroxypropyl)-3(S)-[3'(S)-tetrahydropyranyloxy-1'-trans-octenyl]-4(R)-tetrahydropyranyloxycyclopentane} (374 mg) at a yield of 80% as substantially colorless oily product.

IR (neat): 3350, 2930, 2850, 1450, 1365, 1200 cm$^{-1}$.

NMR δ (CDCl$_3$): 5.35 (m, 2H), 4.50 (m, 2H), 4.00 (m, 2H), 3.60 (m, 8H).

Mass m/z (%): 468 (M$^+$), 450.

EXAMPLE 3

In the method as described in Example 1, the same procedures were carried out in Example 1 except that {1(S)-hydroxymethyl-2(S)-(3'hydroxypropyl)-3(S)-[3'(S)-tetrahydropyranyloxy-1'-trans-octenyl]-4(R)-tetrahydropyranyloxycyclopentane} (374 mg, 0.80 mmol) was employed as the starting material to obtain {3-formyl-6(S)-[3'(S)-tetrahydropyranyloxy-1'-trans-octenyl]-7(R)-tetrahydropyranyloxy-(1S,5S)-cis-bicyclo[3.3.0]oct-2-ene} (232 mg) at a yield of 65% and as substantially colorless oily product.

IR (neat): 2950, 2850, 1680 cm$^{-1}$.

NMR δ (CDCl$_3$): 9.81 (s, 1H), 6.75 (bs, 1H), 5.44 (m, 2H), 4.50 (m, 2H), 3.20–4.10 (m, 7H).

Mass m/z (%): 446 (M+), 361.

EXAMPLE 4

The reaction was carried out following the same procedures as in Reference examples 1 and 2 and Example 1 by using {2(R)-allyl-3(R)-[3'(S)-tetrahydropyranyloxy-1'-trans-octenyl]-4(R)-tetrahydropyranyloxy-1'-cyclopentanone} (868 mg, 2 mmol) to obtain {3-formyl-6(S)-[3'(S)-tetrahydropyranyloxy-1'-trans-octenyl]-7(R)-tetrahydropyranyloxy-(1S,5S)-cis-bicyclo[3.3.0]oct-2-ene} (446 mg, Overall yield: 50%) as substantially colorless oily product.

IR (neat): 2950, 2850, 1680 cm$^{-1}$.

NMR δ (CDCl$_3$): 9.81 (s, 1H), 6.75 (bs, 1H), 5.44 (m, 2H), 4.50 (m, 2H), 3.20–4.10 (m, 7H).

Mass m/z (%): 446 (M+), 361.

EXAMPLE 5

{3-Formyl-6(S)-[3'(S)-hydroxy-1'-trans-octenyl]-7(R)-hydroxy-(1S,5S)-cis-bicyclo[3.3.0]oct-2-ene} (7.8 mg, 0.1 mmol) was dissolved in anhydrous methylene chloride (1 ml), and to the solution was added subsequently dihydropyrane (84 mg, 1 mmol) and catalytic amount of anhydrous p-toluenesulfonic acid and stirred at room temperature for 5 minutes. After the reaction was stopped by adding a saturated aqueous sodium hydrogencarbonate solution, the mixture was extracted with ether. The separated organic layer was washed with a saturated saline solution and dried with anhydrous magnesium sulfate. Evaporation of the solvent, followed by purification through silica gel column chromatography to obtain {3-formyl-6(S)-[3'(S)-tetrahydropyranyloxy-1'-trans-octenyl]-7(R)-tetrahydropyranyloxy-(1S,5S)-cis-bicyclo[3.3.0]oct-2-ene} (42.4 mg, Yield: 95%) as substantially colorless oily product. Spectrum data thereof are agreed with those of the sample obtained in Example 3.

REFERENCE EXAMPLE 4

To a methylene chloride (7 ml) solution of {2(R)-allyl-3(R)-[[3'(R)-[3'(S)-t-butyldimethylsilyloxy-3'-cyclopentyl-1'-trans-propenyl]-4(R)-t-butyldimethylsilyloxy-1-cyclopentanone} (354 mg, 0.72 mmol) was added a zinc-titanium chloride-methylene bromide reagent (Zn-TiCl$_4$-CH$_2$Br$_2$/THF, 3.74 ml, about 1.3 equivalents). The mixture was stirred at the same condition for 30 minutes so that the starting materials were all reacted. Subsequently, the mixture was poured into the two layer system solution comprising ether-saturated aqueous sodium hydrogencarbonate solution so as to stop the reation. Then, an ether layer was separated from the mixture, and an aqueous layer was extracted with ether. The combined ether layers were washed with a saturated aqueous ammonium chloride solution and saturated saline solution, and dried with anhydrous magnesium sulfate. Evaporation of the solvent, followed by purification through silica gel column chromatography to obtain {2(R)-allyl-3(R)-[3'(S)-t-butyldimethylsilyloxy-3'-cyclopentyl-1'-trans-propenyl]-4(R)-t-butyldimethylsilyloxy-1-cyclopentylidene} (326 mg, Yield: 88%) as substantially colorless oily products.

IR (neat): 3078, 2930, 2850, 1648, 1460, 1360, 1247 cm$^{-1}$.

NMR δ (CDCl$_3$): 5.70 (m, 1H), 5.40 (m, 2H), 4.70–5.05 (m, 4H), 4.02 (m, 1H), 3.76 (m, 1H), 2.00–2.60 (m, 6H), 1.38 (m, 9H), 0.88 (s, 18H), 0.02 (s, 12H).

Mass m/z (%): 433 (M+-57), 419, 391.

REFERENCE EXAMPLE 5

To {2(R)-allyl-3(R)-[3'(S)-t-butyldimethylsilyloxy-3'-cyclopentyl-1'-trans-propenyl]-4(R)-t-butyldimethylsilyloxy-1-cyclopentylidene} (698 mg, 1.42 mmol) was added THF solution of 9-borabicyclo[3.3.1]nonane (9-BBN) (7.10 mmol, 14.2 ml) at room temperature, and the mixture was stirred for 3 hours. Then, to the reaction system were gradually added dropwise an aqueous 6 N-NaOH solution (6.9 ml) and an aqueous 30% H$_2$O$_2$ solution (5.8 ml) at room temperature, and the mixture was stirred at 60° C. for 2 hours. The reaction mixture was extracted with ether and the extracted ether layer was washed with an aqueous sodium thiosulfate solution and water. After dryness with anhydrous magnesium sulfate, followed by evaporation of the solvent and purification the residue through silica gel column chromatography to obtain {1(S)-hydroxymethyl-2(S)-(3'-hydroxypropyl)-3(S)-[3'(S)-t-butyldimethylsilyloxy-1'-trans-propenyl]-4(R)-t-butyldimethylsilyloxycyclopentane} (442 mg, Yield: 59%) as colorless oily product.

IR (neat): 3345, 2920, 2850, 1456, 1360, 1246 cm$^{-1}$.

NMR δ (CDCl$_3$): 5.35 (m, 2H), 3.95 (m, 2H), 3.59 (m, 4H), 2.16 (m, 4H), 1.10–1.80 (m, 16H), 0.87 (s, 18H), 0.04 (m, 12H).

Mass m/z (%): 469 (M+-57), 451, 394, 377.

EXAMPLE 6

To a methylene chloride solution (5 ml) of oxalyl chloride (0.46 ml, 5.40 mmol) was added dropwise methylene chloride solution (4 ml) of DMSO (0.83 ml, 11.7 mmol) at −78° C. for 5 minutes, and the mixture was stirred at the same condition for 15 minutes. To the thus prepared mixture was added dropwise a methylene chloride solution (3 ml) of {1(S)-hydroxymethyl-2(S)-(3'-hydroxypropyl)-3(S)-[3'(S)-t-butyldimethylsilyloxy-3'-cyclopentyl-1'-trans-propenyl]-4(R)-t-butyldimethylsilyloxycyclopentane} (473 mg, 0.900 mmol), and the mixture was further stirred at −78° C. for 15 minutes. Under the same condition, triethylamine (2.50 ml, 18.0 mmol) was added thereto, then a cooling bath was removed and the mixture was stirred for 15 minutes. Methylene chloride was distilled out under reduced pressure and to the resultant residue were added benzene (8 ml) and trifluoroacetic acid salt of dibenzylamine (220 mg, 0.900 mmol) and the mixture was stirred at 70° C. for 4 hours. The mixture was diluted with ether, washed successively with an aqueous ammonium chloride solution, a saturated aqueous sodium hydrogencarbonate solution and a saturated saline solution and dried with anhydrous magnesium sulfate. After evaporation of the solvent, the residue was purifired through silica gel column chromatography to obtain {3-formyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (385 mg, Yield: 85%) as substantially colorless oily product.

IR (neat): 2950, 2850, 1675, 1450, 1360, 1250 cm$^{-1}$.

NMR δ (CDCl$_3$): 9.82 (s, 1H), 6.72 (bs, 1H), 5.45 (m, 2H), 4.05 (m, 1H), 3.76 (m, 1H), 3.23 (m, 1H), 1.10–2.80 (m, 15H), 0.87, 0.90 (2s, 18H), 0.03 (s, 12H).

Mass m/z (%): 447 (M+-57), 433, 357, 337, 315, 301, 200, 71.

EXAMPLE 7

{3-Formyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (18.9 mg, 0.0374 mmol) was mixed in a mixed solvent of acetic acid-H$_2$O -tetrahydrofuran (3:1:1) (0.2 ml) and the mixture was stirred at 45° C. for 3 hours. After evaporation of the solvent under reduced pressure, to the residue was added a saturated aqueous sodium hydrogencarbonate solution and extracted with ethyl acetate. The separated organic layer was washed with a saturated saline solution and dried with anhydrous magnesium sulfate. Evaporation of the solvent, followed by purification through silica gel column chromatography to obtain {3-formyl-6(S)-[3'(S)-hydroxy-3'-cyclopentyl-1'-trans-propenyl]-7(R)-hydroxy-(1S,5S)-cis-bicyclo[3.3.0]oct-2-ene} (8.7 mg, Yield: 84%) as substantially colorless oily product.

IR (neat): 3400, 2950, 2850, 1684 cm$^{-1}$.

NMR δ (CDCl$_3$): 9.81 (s, 1H), 6.74 (bs, 1H), 5.45 (m, 2H), 4.10 (m, 1H), 3.80 (m, 1H), 3.23 (m, 1H).

Mass m/z (%): 276 (M+), 258 (M+-H$_2$O).

REFERENCE EXAMPLE 6

In the method as described in Reference examples 4 and 5, the same procedures were carried out as in Reference examples 4 and 5 except that {2(R)-allyl-3(R)-[3'(S)-tetrahydropyranyloxy-3'-cyclopentyl-1'-trans-propenyl]-4(R)-tetrahydropyranyloxy-1-cyclopentanone} (432 mg, 1 mmol) was employed as the starting material to obtain {1(S)-hydroxymethyl-2(S)-(3'-hydroxypropyl)-3(S)-[3'(S)-tetrahydropyranyloxy-3'-cyclopentyl-1'-trans-propenyl]-4(R)-tetrahydropyranyloxycyclopentane} (275 mg) at a yield of 74% as substantially colorless oily product.

IR (neat): 3350, 2930, 2850, 1450, 1365, 1200 cm$^{-1}$.

NMR δ (CDCl$_3$): 5.34 (m, 2H), 4.50 (m, 2H), 4.00 (m, 2H), 3.60 (m, 8H).

Mass m/z (%): 466 (M+), 448.

EXAMPLE 8

In the method as described in Example 3, the same procedures were carried out as in Example 3 except that {1(S)-hydroxymethyl-2(S)-(3'-hydroxypropyl)-3(S)-[3'(S)-tetrahydropyranyloxy-3'-cyclopentyl-1-trans-propenyl]-4(R)-tetrahydropyranyloxycyclopentane} (275 mg, 0.74 mmol) was employed as the starting material to obtain {3-formyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (223 mg) at a yield of 68% as substantially colorless oily product.

IR (neat): 2950, 2850, 1680 cm$^{-1}$.

NMR δ (CDCl$_3$): 9.81 (s, 1H), 6.74 (bs, 1H), 5.45 (m, 2H), 4.48 (m, 2H), 3.20-4.10 (m, 7H).

Mass m/z (%): 444 (M+), 359.

EXAMPLE 9

The reaction was carried out following the same procedures as in Reference examples 4 and 5 and Example 8 by using {2(R)-allyl-3(R)-[3'(S)-tetrahydropyranyloxy-3'-cyclopentyl-1'-trans-propenyl]-4(R)-tetrahydropyranyloxy-1-cyclopentanone} (864 mg, 2 mmol) to obtain {3-formyl-6(S)-[3'(S)-tetrahydropyranyloxy-3'-cyclo-pentyl-1'-transpropenyl]-7(R)-tetrahydropyranyloxy-(1S,5S)-cis-bicyclo-[3.3.0]oct-2-ene} (408 mg, Overall yield: 46%) as substantially colorless oily product.

IR (neat): 2950, 2850, 1680 cm$^{-1}$.

NMR δ (CDCl$_3$): 9.81 (s, 1H), 6.74 (bs, 1H), 5.45 (m, 2H), 4.48 (m, 2H), 3.20-4.10 (m, 7H).

Mass m/z (%): 444 (M+), 359.

EXAMPLE 10

{3-Formyl-6(S)-[3'(S)-hydroxy-3'-cyclopentyl-1'-transpropenyl]-7(R)-hydroxy-(1S,5S)-cis-bicyclo[3.3.0]oct-2-ene} (27.6 mg, 0.1 mmol) was dissolved in anhydrous methylene chloride (1 ml), and to the solution was added subsequently dihydropyrane (84 mg, 1 mmol) and catalytic amount of anhydrous p-toluenesulfonic acid and stirred at room temperature for 5 minutes. After the reaction was stopped by adding a saturated aqueous sodium hydrogencarbonate solution, the mixture was extracted with ether. The separated organic layer was washed with a saturated saline solution and dried with anhydrous magnesium sulfate. Evaporation of the solvent, followed by purification through silica gel column chromatography to obtain {3-formyl-6(S)-[3'(S)-tetrahydropyranyloxy-3'-cyclopentyl-1'-trans-propenyl]-7(R)-tetrahydropyranyloxy(1S,5S)-cis-bicyclo[3.3.0]oct-2-ene} (39.5 mg, Yield: 89%) as substantially colorless oily product. Various spectrum data thereof are agreed with those of the sample obtained in Example 8.

EXAMPLE 11

3-Carboxypropyltriphenylphosphonium bromide (321 mg, 0.748 mmol) was suspended in THF (3.0 ml), and to the suspension was added potassium t-butoxide (167 mg, 1.49 mmol) and the mixture was stirred at room temperature for 10 minutes. To the obtained yield compound having reddish orange color was added a THF (1.5 ml) solution of {3-formyl-6(S)-[3'(S)-t-butyldimethylsilyloxy-1'-transoctenyl]-7(R)-t-butyldimethylsilyloxy-(1S,5S)-cis-bicyclo[3.3.0]oct-2-ene} (189 mg, 0.374 mmol), and the mixture was stirred for 30 minutes. The mixture was diluted with ether, added a 10% aqueous HCl solution and after it was confirmed that the mixture was acidic (pH=4), an ether layer was separated therefrom. After the separated aqueous layer was extracted with ether, the ether layers were combined, washed with a saturated aqueous NaCl solution and dried with anhydrous magnesium sulfate. After evaporation of the solvent, the resultant residue was dissolved in small amount of ether and added thereof an ether solution of diazomethane to obtain a methyl ester derivative. Evaporation of the solvent, followed by purification and separation through silica gel column chromatography to obtain {3-(4'-methoxycarbonyl-1'-butenyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (194 mg, Yield: 88%) as substantially colorless oily products.

IR (neat): 2950, 2850, 1750, 1460, 1360, 1250 cm$^{-1}$.

NMR δ (CDCl$_3$): 6.27 (d, J=16 Hz, 2/5H, trans), 6.02 (d, J=11 Hz, 3/5H, cis), 5.51 (m, 4H), 4.07 (m, 1H), 3.70 (m, 1H), 3.69 (s, 3H), 2.97 (m, 1H), 1.10-2.70 (m, 16H), 0.87, 0.90 (2s, 21H), 0.03 (s, 12H).

Mass m/z (%): 590 (M+), 534, 533, 519, 458, 427, 401, 301, 75, 73.

$[\alpha]_D^{20} = -37°$ (c=0.614, CHCl$_3$).

EXAMPLE 12

To a THF (0.5 ml) solution of {3-(4'-methoxycarbonyl-1'-butenyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (31 mg, 0.05 mmol) was added a solution of tetrabutylammonium fluoride dissolved in THF (0.16 ml, 1M solution), and the mixture was stirred at room temperature for 15 hours. After the reaction was stopped by adding a saturated aqueous ammonium chloride solution, THF was distilled out under reduced pressure. The resultant aqueous layer was extracted with ethyl acetate, and the separated organic layer was washed with a saturated saline solution and dried with anhydrous magnesium sulfate. Evaporation of the solvent, followed by purification through silica gel column chromatography to obtain {3-(4'-methoxycarbonyl-1'-butenyl)-6(S)-[3'(S)-hydroxy-trans-octenyl]-7(R)-hydroxy-(1S,5S)-cis-bicyclo[3.3.0]oct-2-ene} (15 mg, Yield: 79%) as colorless caramel.

IR (neat): 3400, 2950, 1742 cm$^{-1}$.

NMR δ (CDCl$_3$): 6.30 (d, J=16 Hz, ⅓H, trans), 6.02 (d, J=11 Hz, 2/3H, cis), 5.60 (m, 3H), 5.40 (m, 1H), 4.10 (m, 1H), 3.80 (m, 1H), 3.70 (s, 3H), 3.02 (m, 1H).

Mass m/z (%): 362 (M+, 7), 344 (44), 326 (19), 300 (37), 220 (54), 178 (55), 168 (41), 43 (100). $[\alpha]_D^{20} = -35°$ (c=0.466, MeOH).

EXAMPLE 13

In the method as described in Example 11, the same procedures were carried out as in Example 11 except that {3-formyl-6(S)-[3'(S)-tetrahydropyranyloxy-1'-trans-octenyl]-7(R)-tetrahydropyranyloxy-(1S,5S)-cis-bicyclo[3.3.0]oct-2-ene} (446 mg, 1 mmol) was employed as the starting material to obtain {3-(4'-methoxycarbonyl-1'-butenyl)-6(S)-[3'(S)-tetrahydropyranyloxy-1'-trans-octenyl]-7(R)-tetrahydropyranyloxy-(1S,5S)-cis-bicyclo[3.3.0]oct-2-ene} (477 mg, Yield: 90%) as substantially colorless oily product.

IR (neat): 2950, 2850, 1745 cm$^{-1}$.

NMR δ (CDCl$_3$): 6.25 (d, J=16 Hz, ⅓H, trans), 6.02 (d, J=11 Hz, 2/3H, cis), 5.50 (m, 4H), 4.60 (m, 2H), 3.40–4.10 (m, 6H), 3.69 (s, 3H), 2.97 (m, 1H), 0.87 (t, J=7 Hz, 3H).

Mass m/z (%): 530 (M+), 499, 445.

EXAMPLE 14

{3-(4'-Methoxycarbonyl-1'-butenyl)-6-(S)-[3'(S)-tetrahydropyranyloxy-1'-trans-octenyl]-7(R)-tetrahydropyranyloxy-(1S,5S)-cis-bicyclo[3.3.0]oct-2-ene} (470 mg, 0.89 mmol) was dissolved in a mixed solvent of acetic acid (4.7 ml), water (1.6 ml) and THF (1.6 ml), and heated at atmospheric temperature of 45° C. for 6 hours. After evaporation of acetic acid under reduced pressure, to the residue was added a saturated aqueous sodium hydrogencarbonate solution and extracted with ethyl acetate. The separated organic layer was washed with saturated saline solution, and dried with anhydrous magnesium sulfate. Evaporation of the solvent, followed by purification through silica gel column chromatography to obtain {3-(4'-methoxycarbonyl-1'-butenyl)-6(S)-[3'(S)-hydroxy-1'-trans-octenyl]-7(R)-hydroxy-(1S,5S)-cis-bicyclo[3.3.0]oct-2-ene} (261 mg, Yield: 81%) as colorless caramel. Spectrum data thereof are agreed with those of the sample obtained in Example 12.

EXAMPLE 15

{3-(4'-Methoxycarbonyl-1'-butenyl)-6(S)-[3'(S)-hydroxy-1'-trans-octenyl]-7(R)-hydroxy-(1S,5S)-cis-bicyclo[3.3.0]oct-2-ene} (15 mg, 0.04 mmol) was dissolved in methanol (0.3 ml). To the solution was added a 10% aqueous sodium hydroxide solution (0.3 ml) at 0° C. After stirring at 0° C. for 16 hours, the mixture was neutralized with a 10% aqueous hydrochloric acid solution under cooling. After evaporation of methanol under reduced pressure, the residue was adjusted to pH 3 to 4 and extracted with ethyl acetate. The extract was dried with anhydrous magnesium sulfate and distilled out the solvent to obtain {3-(4'-carboxy-1'-butenyl)-6(S)-[3'(S)-hydroxy-1'-trans-octenyl]-7(R)-hydroxy-(1S,5S)-cis-bicyclo[3.3.0]oct-2-ene} (14 mg, Yield: 100%) as colorless caramel.

IR (neat): 3350, 1720, 1090, 970 cm$^{-1}$.

NMR δ (CDCl$_3$): 6.34 (d, J=16 Hz, ⅓H), 6.06 (d, J=11 Hz, 2/3H), 5.65 (m, 3H), 5.45 (m, 1H), 3.10 (m, 1H).

EXAMPLE 16

3-Carboxypropyltriphenylphosphonium bromide (321 mg, 0.748 mmol) was suspended in THF (3.0 ml), and to the suspension was added potassium t-butoxide (167 mg, 1.49 mmol) and the mixture was stirred at room temperature for 10 minutes. To the obtained yield compound having reddish orange color was added THF (1.5 ml) solution of {3-formyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (189 mg, 0.374 mmol), and the mixture was stirred for 30 minutes. The mixture was diluted with ether, added a 10% aqueous HCl solution and after it was confirmed that the mixture was acidic (pH=4), an ether layer was separated therefrom. After the separated aqueous layer was extracted with ether, the ether layers were combined, washed with a saturated aqueous NaCl solution and dried with anhydrous magnesium sulfate. After evaporation of the solvent, the resultant residue was dissolved in small amount of ether and added an ether solution of diazomethane to obtain a methyl ester derivative. Evaporation of the solvent, followed by purification and separation through silica gel column chromatography to obtain {3-(4'-methoxycarbonyl-1'-butenyl)-6(S)-[3'(S)-t-butyldimethylsilyloxy-3'-cyclopentyl-trans-propenyl]-7(R)-t-butyldimethylsilyloxy-(1S,5S)-cis-bicyclo[3.3.0]oct-2-ene} (175 mg, Yield: 80%) as substantially colorless oily products.

IR (neat): 2950, 2850, 1745, 1460, 1358, 1240 cm$^{-1}$.

NMR δ (CDCl$_3$): 6.25 (d, J=16 Hz, 2/5H, trans), 6.01 (d, J=11 Hz, 3/5H, cis), 5.50 (m, 4H), 4.07 (m, 1H), 3.69 (m, 1H), 3.68 (s, 3H), 2.98 (m, 1H), 1.10–2.70 (m, 17H), 0.87, 0.90 (2s, 18H), 0.03 (s, 12H).

Mass m/z (%): 588 (M+), 532, 531, 517.

$[\alpha]_D^{20} = -37°$ (c=1.618, CHCl$_3$).

EXAMPLE 17

To a THF (1.5 ml) solution of {3-(4'-methoxycarbonyl-1'-butenyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (81 mg, 0.14 mmol) was added a solution of tetrabutylammonium fluoride dissolved in THF (0.42 ml, 1M solution), and the mixture was stirred at room temperature for 16 hours. After the reaction was stopped by adding a saturated aqueous ammonium chloride solution, THF was distilled out under reduced pressure. The resultant aqueous layer was extracted with ethyl acetate, and the separated organic layer was washed with a saturated saline solution and dried with anhydrous magnesium sulfate. Evaporation of the solvent, followed by purification through silica gel column chromatography to obtain {3-(4'-methoxycarbonyl-1'-butenyl)-6(S)-[3'(S)-hydroxy-3'-cyclopentyl-1'-trans-propenyl]-7(R)-hydroxy-(1S,5S)-cis-bicyclo[3.3.0]oct-2-ene} (49 mg, Yield: 100%) as colorless caramel.

IR (neat): 3400, 1740, 1430, 1160, 1090, 965 cm$^{-1}$.

NMR δ (CDCl$_3$): 6.22 (d, J=16 Hz, ⅓H, trans), 5.95 (d, J=11 Hz, 2/3H, cis), 5.13–5.74 (m, 4H, olefinic proton), 3.66 (s, 3H), 3.50–4.00 (m, 2H), 3.02 (m, 1H).

Mass m/z (%): 360 (M+), 342 (M+-H$_2$O), 324 (M+-2H$_2$O), 298, 273.

$[\alpha]_D^{20} = -30°$ (c=1.16, MeOH).

EXAMPLE 18

In the method as described in Example 16, the same procedures were carried out as in Example 16 except that {3-formyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (408 mg, 0.92 mmol) was employed as the starting material to obtain {3-(4'-methoxycarbonyl-1'-butenyl)-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (447 mg, Yield: 92%) as substantially colorless oily product.

IR (neat): 2950, 2850, 1744 cm$^{-1}$.

NMR δ (CDCl$_3$): 6.24 (d, J=16 Hz, ⅓H, trans), 6.01 (d, J=11 Hz, 2/3H, cis), 5.50 (m, 4H), 4.60 (m, 2H), 3.50–4.10 (m, 6H), 3.68 (s, 3H), 2.98 (m, 1H).

Mass m/z (%): 528 (M+), 497, 443.

EXAMPLE 19

{3-(4'-Methoxycarbonyl-1'-butenyl)-6-(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (500 mg, 0.95 mmol) was dissolved in a mixed solvent of acetic aicd (4.7 ml), water (1.6 ml) and THF (1.6 ml), and heated at atmospheric temperature of 45° C. for 6 hours. After evaporation of acetic acid under reduced pressure, to the residue was added a saturated aqueous sodium hydrogencarbonate solution and extracted with ethyl acetate. The separated organic layer was washed with saturated saline solution, and dried with anhydrous magnesium sulfate. Evaporation of the solvent, followed by purification through silica gel column chromatography to obtain {3-(4'-methoxycarbonyl-1'-butenyl)-6(S)-[3'(S)-hydroxy-3'-cyclopentyl-1'-trans-propenyl]-7(R)-hydroxy(1S,5S)-cis-bicyclo[3.3.0]oct-2-ene} (308 mg, Yield: 90%) as colorless caramel. Spectrum data thereof are agreed with those of the sample obtained in Example 17.

EXAMPLE 20

{3-(4'-Methoxycarbonyl-1'-butenyl)-6(S)-[3'(S)-hydroxy-3'-cyclopentyl-1'-trans-propenyl]-7(R)-hydroxy-(1S,5S)-cis-bicyclo[3.3.0]oct-2-ene} (50 mg, 0.14 mmol) was dissolved in methanol (1.1 ml). To the solution was added a 10% aqueous sodium hydroxide solution (1.1 ml) at 0° C. After stirring at 0° C. for 16 hours, the mixture was neutralized with a 10% aqueous hydrochloric acid solution under cooling. After evaporation of methanol under reduced pressure, the residue was adjusted to pH 3 to 4 and extracted with ethyl acetate. The extract was dried with anhydrous magnesium sulfate and distilled out the solvent to obtain {3-(4'-carboxy-1'-butenyl)-6(S)-[3'(S)-hydroxy-3'-cyclopentyl-1'-trans-propenyl]-7(R)-hydroxy-(1S,5S)-cis-bicyclo[3.3.0]oct-2-ene} (43 mg, Yield: 89%) as colorless caramel.

IR (neat): 3350, 1715, 1085, 970 cm$^{-1}$.

NMR δ (CDCl$_3$): 6.32 (d, J=16 Hz, ⅓H), 6.04 (d, J=12 Hz, ⅔H), 5.64 (m, 3H), 5.44 (m, 1H), 3.10 (m, 1H).

REFERENCE EXAMPLE 7

To a benzene (0.9 ml) solution of {3-(4'-methoxycarbonyl-1'-butenyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (48 mg, 0.081 mmol) was added RhCl(Ph$_3$P)$_3$ (10 mg), and the mixture was stirred, under hydrogen atmosphere (ordinary pressure), at room temperature for an hour and then at 45° C. for 1.5 hours. After the catalyst was removed by passing short length silica gel column, the resultant residue was purifired again through silica gel column chromatography to obtain 45 mg of colorless oily product. To the product was added a THF solution (0.8 ml, 1M concentration) of tetrabutylammonium fluoride and the mixture was stirred at room temperature for 12 hours to remove silyl ether. Evaporation of the solvent, followed by purification through silica gel column chromatography to obtain {3-(4'-methoxycarbonylbutyl)-6(S)-[3'(S)-hydroxy-1'-trans-octenyl]-7(R)-hydroxy-(1S,5S)-cis-bicyclo[3.3.0]oct-2-ene} (20 mg, Yield: 69%).

IR (neat): 3400, 2970, 2930, 2870, 1742 cm$^{-1}$.

NMR δ (CDCl$_3$): 5.60 (m, 2H), 5.33 (bs, 1H), 4.12 (m, 1H), 3.80 (m, 1H), 3.69 (s, 3H), 3.00 (m, 1H).

Mass m/z (%): 346 (M+-H$_2$O), 328, 315, 302, 275, 247, 232, 199, 193, 180, 179.

REFERENCE EXAMPLE 8

{3-(4'-Metoxycarbonylbutyl)-6(S)-[3'(S)-hydroxy-1'-trans-octenyl]-7(R)-hydroxy-(1S,5S)-cis-bicyclo[3.3.0]oct-2-ene} (10 mg, 0.027 mmol) was dissolved in methanol (0.3 ml). To the solution was added a 10% aqueous sodium hydroxide solution (0.2 ml) at 0° C. After stirring at 0° C. for 9 hours, the mixture was neutralized with a 10% aqueous hydrochloric acid solution under cooling. After evaporation of methanol under reduced pressure, the residue was adjusted to pH 3 to 4 and extracted with ethyl acetate. After dryness with anhydrous magnesium sulfate, followed by evaporation of the solvent to obtain [9(0)-methano-Δ$^{6(9\alpha)}$-PGI$_1$] (10 mg, Yield: 100%).

IR (neat): 3350, 2910, 2850, 1700, 1450, 1250 cm$^{-1}$.

NMR δ (CDCl$_3$): 5.60 (m, 2H), 5.31 (bs, 1H), 4.11 (m, 1H), 3.80 (m, 1H), 3.00 (m, 1H), 0.90 (t, J=6 Hz, 3H).

Mass (CI, NH$_3$) m/z: 368 (M+ +NH$_4$).

Melting point: 73° to 79° C.

$[\alpha]_D^{20} = +16°$ (c=0.25, MeOH).

REFERENCE EXAMPLE 9

To a benzene (0.5 ml) solution of {3-(4'-methoxycarbonyl-1'-butenyl)-6(S)-[3'(S)-hydroxy-1'-trans-octenyl]-7(R)-hydroxy-(1S,5S)-cis-bicyclo[3.3.0]oct-2-ene} (15 mg, 0.041 mmol) was added RhCl(Ph$_3$P)$_3$ (5 mg), and the mixture was stirred, under hydrogen atmosphere (ordinary pressure), at room temperature for an hour and then at 45° C. for 1.5 hours. After the catalyst was removed by passing short length silica gel column, the resultant residue was purifired again through silica gel column chromatography to obtain 9 mg of colorless oily product. The thus obtained product was dissolved in methanol (0.1 ml). To the solution was added a 10% aqueous sodium hydroxide solution (0.1 ml) at 0° C. After stirring at 0° C. for 9 hours, the mixture was neutralized with a 10% aqueous hydrochloric acid solution at 0° C. After evaporation of methanol under reduced pressure, the residue was adjusted to pH 3 to 4 and extracted with ethyl acetate. After dryness with anhydrous magnesium sulfate followed by evaporation of the solvent to obtain {3-(4'-carboxybutyl)-6(S)-[3'(S)-hydroxy-1'-trans-octenyl]-7(R)-hydroxy-(1S,5S)-cis-bicyclo[3.3.0]oct-2-ene} (9 mg) as colorless solid. Spectrum data thereof are agreed with those of the sample obtained in Reference example 8.

REFERENCE EXAMPLE 10

To a benzene (0.5 ml) solution of {3-(4'-carboxy-1'-butenyl)-6(S)-[3'(S)-hydroxy-1'-trans-octenyl]-7(R)-hydroxy-(1S,5S)-cis-bicyclo[3.3.0]oct-2-ene} (14 mg, 0.041 mmol) was added RhCl(Ph$_3$P)$_3$ (5 mg), and the mixture was stirred, under hydrogen atmosphere (ordinary pressure), at room temperature for an hour and then at 45° C. for 1.5 hours. After the catalyst was removed by short length silica gel column, the resultant residue was purifired again through silica gel column chromatography to obtain 6 mg of {3-(4'-carboxybutyl)-6(S)-[3'(S)-hydroxy-1'-trans-octenyl]-7(R)-hydroxy-(1S,5S)-cis-bicyclo[3.3.0]oct-2-ene} as colorless solid. Spectrum data thereof are agreed with those of the sample obtained in Reference example 8.

REFERENCE EXAMPLE 11

To a benzene (0.9 ml) solution of {3-(4'-methoxycarbonyl-1'-butenyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (47 mg, 0.081 mmol) was added RhCl(Ph$_3$P)$_3$ (10 mg), and the mixture was stirred, under hydrogen atmosphere (ordinary pressure), at room temperature for an hour and then at 45° C. for 1.5 hours. After the catalyst was removed by passing short length silica gel column, the resultant residue was purifired again through silica gel column chromatography to obtain 42 mg of colorless oily product. To the product was added a THF solution (0.8 ml, 1M concentration) of tetrabutylammonium fluoride and the mixture was stirred at room temperature for 12 hours to remove silyl ether. Evaporation of the solvent, followed by purification through silica gel column chromatography to obtain {3-(4'-methoxycarbonylbutyl)-6(S)-[3'(S)-hydroxy-3'-cyclopentyl-1'-trans-propenyl]-7(R)-hydroxy-(1S,5S)-cis-bicyclo[3.3.0]oct-2-ene} (17 mg, Yield: 60%).

IR (neat): 3400, 2960, 2880, 1740 cm$^{-1}$.

NMR δ (CDCl$_3$): 5.61 (m, 2H), 5.32 (bs, 1H), 3.85 (m, 2H), 3.67 (s, 3H), 3.00 (m, 1H), 1.10–2.60 (m, 26H).

Mass m/z (%): 344 (M+-18), 326 (M+-36), 300, 275, 243, 232, 225, 199, 193, 183, 181, 180, 179, 141, 119, 117, 105, 93, 91, 81, 79, 69, 67, 55, 41.

REFERENCE EXAMPLE 12

{3-(4'-Metoxycarbonylbutyl)-6(S)-[3'(S)-hydroxy-3'-cyclopentyl-1'-trans-propenyl]-7(R)-hydroxy-(1S,5S)-cis-bicyclo[3.3.0]oct-2-ene} (10 mg, 0.027 mmol) was dissolved in methanol (0.3 ml). To the solution was added a 10% aqueous sodium hydroxide solution (0.2 ml) at 0° C. After stirring at 0° C. for 9 hours, the mixture was neutralized with a 10% aqueous hydrochloric acid solution under cooling. After evaporation of methanol under reduced pressure, the residue was adjusted to pH 3 to 4 and extracted with ethyl acetate. After the extract was dried with anhydrous magnesium sulfate, then distilled out the solvent to obtain {3-(4'-carboxybutyl)-6(S)-[3'(S)-hydroxy-3'-cyclopentyl-1'-trans-propenyl]-7(R)-hydroxy-(1S,5S)-cis-bicyclo[3.3.0]oct-2-ene} (10 mg, Yield: 100%) as colorless solids. Recrystallization from ethyl acetate-hexane of the solids yielded colorless powders having melting point of 115° to 116° C.

IR (KBr): 3430 (OH), 2960, 1700, 1655 cm$^{-1}$.

NMR δ (CDCl$_3$): 5.60 (m, 2H), 5.32 (bs, 1H), 3.90 (m, 2H), 3.00 (m, 1H), 1.00–2.70 (m, 25H).

Mass (CI, NH$_3$) m/z: 366 (M+ +NH$_4$)

REFERENCE EXAMPLE 13

To a benzene (0.5 ml) solution of {3-(4'-methoxycarbonyl-1'-butenyl)-6(S)-[3'(S)-hydroxy-3'-cyclopentyl-1'-trans-propenyl]-7(R)-hydroxy-(1S,5S)-cis-bicyclo[3.3.0]oct-2-ene} (15 mg, 0.041 mmol) was added RhCl(Ph$_3$P)$_3$ (5 mg), and the mixture was stirred, under hydrogen atmosphere (ordinary pressure), at room temperature for an hour and then at 45° C. for 1.5 hours. After the catalyst was removed by passing short length silica gel column, the resultant residue was purifired again through silica gel column chromatography to obtain 8 mg of colorless viscous oil. The thus obtained oil was dissolved in methanol (0.1 ml). To the solution was added a 10% aqueous sodium hydroxide solution (0.1 ml) at 0° C. After stirring at 0° C. for 9 hours, the mixture was neutralized with a 10% aqueous hydrochloric acid solution under cooling. After evaporation of methanol under reduced pressure, the residue was adjusted to pH 3 to 4 and extracted with ethyl acetate. After dryness with anhydrous magnesium sulfate followed by evaporation of the solvent to obtain {3-(4'-carboxybutyl)-6(S)-[3'(S)-hydroxy-3'-cyclopentyl-1'-trans-propenyl]-7(R)-hydroxy-(1S,5S)-cis-bicyclo[3.3.0]oct-2-ene} (8 mg) as colorless solid. Spectrum data thereof are agreed with those of the sample obtained in Reference example 12.

REFERENCE EXAMPLE 14

To a benzene (0.5 ml) solution of {3-(4'-carboxy-1'-butenyl)-6(S)-[3'(S)-hydroxy-3'-cyclopentyl-1'-trans-propenyl]-7(R)-hydroxy-(1S,5S)-cis-bicyclo[3.3.0]oct-2-ene} (14 mg, 0.041 mmol) was added RhCl(Ph$_3$P)$_3$ (5 mg), and the mixture was stirred, under hydrogen atmosphere (ordinary pressure), at room temperature for an hour and then at 45° C. for 1.5 hours. After the catalyst was removed by passing short length silica gel column, the resultant residue was purifired again through silica gel column chromatography to obtain 7 mg of {3-(4'-carboxybutyl)-6(S)-[3'(S)-hydroxy-3'-cyclopentyl-1'-trans-propenyl]-7(R)-hydroxy-(1S,5S)-cis-bicyclo[3.3.0]oct-2-ene} as colorless solid. Spectrum data thereof are agreed with those of the sample obtained in Reference example 12.

EXAMPLE 21

To a toluene (3.5 ml) solution of {3-formyl-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (420 mg, 0.83 mmol) was added diisobutylaluminum hydride (1.25 mmol, 0.71 ml, 1.76M hexane solution) at −78° C. and the mixture was stirred for 90 minutes. To the mixture was added dropwise methanol until the generation of hydrogen was stopped, and the mixture was diluted with ether. To the mixture was further added a saturated saline solution and stirring was continued until an organic layer became transparent. After an ether layer was separated from the mixture, extraction of an aqueous layer with ether was repeated. The separated ether layer and the extracts were combined and dried with anhydrous magnesium sulfate. After evaporation of the solvent, the residue was purified through silica gel column chromatography to obtain {3-hydroxymethyl-6(S)-[3′(S)-t-butyldimethylsilyloxy-1′-trans-octenyl]-7(R)-t-butyldimethylsilyloxy-(1S,5S)-cis-bicyclo[3.3.0]oct-2-ene} (373 mg, Yield: 88%) as substantially colorless oily product.

IR (neat): 3350 cm$^{-1}$.

NMR δ (CDCl$_3$): 5.47 (m, 3H), 4.13 (m, 3H), 3.73 (m, 1H), 2.97 (m, 1H).

Mass m/z: 451 (M$^+$-57).

EXAMPLE 22

In the method as described in Example 21, the same procedures were carried out as in Example 21 except that {3-formyl-6(S)-[3′(S)-tetrahydropyranyloxy-1′-trans-octenyl]-7(R)-tetrahydropyranyloxy-(1S,5S)-cis-bicyclo-[3.3.0]oct-2-ene} (370 mg, 0.83 mmol) was employed as the starting material to obtain {3-hydroxymethyl-6(S)-[3′(S)-tetrahydropyranyloxy-1′-trans-octenyl]-7(R)-tetrahydropyranyloxy-(1S,5S)-cis-bicyclo[3.3.0]oct-2-ene} (316 mg, Yield: 85%) as substantially colorless oily product.

IR (neat): 3345 cm$^{-1}$.

NMR δ (CDCl$_3$): 5.45 (m, 3H), 4.55 (m, 2H), 4.10 (m, 3H), 3.50–4.00 (m, 5H), 2.98 (m, 1H).

Mass m/z: 364 (M$^+$-84).

EXAMPLE 23

To a pyridine (1.5 ml) solution of {3-hydroxymethyl-6(S)-[3′(S)-t-butyldimethylsilyloxy-1′-trans-octenyl]-7(R)-t-butyldimethylsilyloxy-(1S,5S)-cis-bicyclo[3.3.0]oct-2-ene} (97 mg, 0.19 mmol) were added acetic anhydride (0.29 mmol, 27 μl) and catalytic amount of 4-dimethylaminopyridine at room temperature, and the mixture was stirred for 30 minutes under the same conditions. To the mixture was added a saturated aqueous copper sulfate solution and the mixture was extracted with ether. The separated ether layer was washed with water and then dried with anhydrous magnesium sulfate. After evaporation of the solvent, the residue was purified through silica gel column chromatography to obtain {3-acetoxymethyl-6(S)-[3′(S)-t-butyldimethylsilyloxy-1′-trans-octenyl]-7(R)-t-butyldimethylsilyloxy-(1S,5S)-cis-bicyclo-[3.3.0]oct-2-ene} (104 mg, Yield: 100%) as colorless oily product.

IR (neat): 1755 cm$^{-1}$.

NMR δ (CDCl$_3$): 5.47 (m, 3H), 4.55 (s, 2H), 4.01 (m, 1H), 3.68 (m, 1H), 2.93 (m, 1H), 2.05 (s, 3H).

Mass m/z: 493 (M$^+$-57).

EXAMPLE 24

In the method as described in Example 23, the same procedures were carried out as in Example 23 except that {3-hydroxymethyl-6(S)-[3′(S)-tetrahydropyranyloxy-1′-trans-octenyl]-7(R)-tetrahydropyranyloxy-(1S,5S)-cisbicyclo[3.3.0]oct-2-ene} (85 mg, 0.19 mmol) was employed as the starting material to obtain {3-acetoxymethyl-6(S)-[3′(S)-tetrahydropyranyloxy-1′-trans-octenyl]-7(R)-tetrahydropyranyloxy-(1S,5S)-cis-bicyclo[3.3.0]oct-2-ene} (93 mg, Yield: 100%) as substantially colorless oily product.

IR (neat): 1750 cm$^{-1}$.

NMR δ (CDCl$_3$): 5.45 (m, 3H), 4.55 (m, 4H), 4.05 (m, 1H), 3.40–4.00 (m, 5H), 2.91 (m, 1H), 2.05 (s, 3H).

Mass m/z: 406 (M$^+$-84).

EXAMPLE 25

To a suspension of cuprous iodide (163 mg, 0.85 mmol) in ethyl ether (1.5 ml) was added freshly prepared 3-butenyl lithium (1.70 mmol, 1,31 ml, 1.30M hexane solution) at −30° C., and the mixture was stirred for 30 minutes. After the mixture was cooled to −78° C., an ethyl ether (1 ml) solution of {3-acetoxymethyl-6(S)-[3′(S)-t-butyl-dimethylsilyloxy-1′-trans-octenyl]-7(R)-t-butyldimethylsilyloxy-(1S,5S)-cis-bicyclo[3.3.0]oct-2-ene} (213 mg, 0.39 mmol) was added thereto and the mixture was stirred for an hour at the same conditions. After further continuation of stirring at room temperature for 0.5 hour, the reaction was stopped by adding a saturated aqueous ammonium chloride solution. The reaction mixture was extracted with ether, and the separated ether layer was washed with a saturated saline solution and dried with anhydrous magnesium sulfate. After evaporation of the solvent, the residue was purified through silica gel column chromatography to obtain {3-(4′-pentenyl)-6(S)-[3′(S)-t-butyldimethylsilyloxy-1′-trans-octenyl]-7(R)-t-butyldimethylsilyloxy-(1R,5R)-cis-bicyclo[3.3.0]oct-2-ene} (154 mg, Yield: 73%) as substantially colorless oily product. The thus obtained product contained about 10% of {2-(3′-butenyl)-3-methylidene-6(S)-[3′(S)-t-butyldimethylsilyloxy-1′-trans-octenyl]-(1S,5S)-cis-bicyclo[3.3.0]octane}.

IR (neat): 1645 cm$^{-1}$.

NMR δ (CDCl$_3$): 5.40–6.05 (m, 1H), 5.35 (m, 2H), 5.20 (bs, about 1H), 4.90 (m, 2H), 4.00 (m, 1H), 3.60 (m, 1H), 2.90 (m, about 1H).

Mass m/z: 489 (M$^+$-57).

EXAMPLE 26

In the method as described in Example 25, the same procedures were carried out as in Example 25 except that {3-acetoxymethyl-6(S)-[3′(S)-tetrahydropyranyloxy-1′-trans-octenyl]-7(R)-tetrahydropyranyloxy-(1S,5S)-cisbicyclo[3.3.0]oct-2-ene} (191 mg, 0.39 mmol) was employed as the starting material to obtain {3-(4′-pentenyl)-6(S)-[ 3′(S)-tetrahydropyranyloxy-1′-trans-octenyl]-7(R)-tetrahydropyranyloxy-(1S,5S)-cis-bicyclo[3.3.0]oct-2-ene} (133 mg, Yield: 70%) as substantially colorless oily product. The thus obtained product contained about 10% of {2-(3′-butenyl)-3-methylidene-6(S)-[3′(S)-tetrahydropyranyloxy-1′-trans-octenyl]-(1S,5S)-cis-bicyclo[3.3.0]octane}.

IR (neat): 1645 cm$^{-1}$.

NMR δ (CDCl$_3$): 5.40–6.05 (m, 1H), 5.35 (m, 2H), 5.20 (bs, about 1H), 4.90 (m, 2H), 4.55 (m, 2H), 4.00 (m, 1H), 3.40–3.70 (m, 5H), 2.90 (m, about 1H).

Mass m/z: 402 (M$^+$-84).

EXAMPLE 27

In the method as described in Example 21, the same procedures were carried out as in Example 21 except that {3-formyl-6(S)-[3′(S)-t-butyldimethylsilyloxy-3′-cyclopentyl-1′-trans-propenyl]-7(R)-t-butyldimethylsilyloxy-(1S,5S)-cis-bicyclo[3.3.0]oct-2-ene} (418 mg, 0.83 mmol) was employed as the starting material to obtain {3-hydroxymethyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (372 mg, Yield: 86%) as substantially colorless oily product.

IR (neat): 3350 cm$^{-1}$.

NMR δ (CDCl$_3$): 5.45 (m, 3H), 4.13 (m, 3H), 3.70 (m, 1H), 2.98 (m, 1H).

Mass m/z: 449 (M$^+$-57).

EXAMPLE 28

In the method as described in Example 21, the same procedures were carried out as in Example 21 except that {3-formyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (368 mg, 0.83 mmol) was employed as the starting material to obtain {3-hydroxymethyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (306 mg, Yield: 83%) as substantially colorless oily product.

IR (neat): 3345 cm$^{-1}$.

NMR δ (CDCl$_3$): 5.45 (m, 3H), 4.55 (m, 2H), 4.10 (m, 3H), 3.50-4.00 (m, 5H), 2.98 (m, 1H).

Mass m/z: 362 (M$^+$-84).

EXAMPLE 29

In the method as described in Example 23, the same procedures were carried out as in Example 23 except that {(3-hydroxymethyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (96 mg, 0.19 mmol) was employed as the starting material to obtain {3-acetoxymethyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (103 mg, Yield: 100%) as colorless oily product.

IR (neat): 1755 cm$^{-1}$.

NMR δ (CDCl$_3$): 5.47 (m, 3H), 4.54 (s, 2H), 4.00 (m, 1H), 3.68 (m, 1H), 2.92 (m, 1H), 2.05 (s, 3H).

Mass m/z: 492 (M$^+$-57).

EXAMPLE 30

In the method as described in Example 23, the same procedures were carried out as in Example 23 except that {3-hydroxymethyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (84 mg, 0.19 mmol) was employed as the starting material to obtain {3-acetoxymethyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (91 mg, Yield: 100%) as substantially colorless oily product.

IR (neat): 1750 cm$^{-1}$.

NMR δ (CDCl$_3$): 5.45 (m, 3H), 4.55 (m, 4H), 4.05 (m, 1H), 3.40-4.00 (m, 5H), 2.91 (m, 1H), 2.05 (s, 3H).

Mass m/z: 404 (M$^+$-84).

EXAMPLE 31

In the method as described in Example 25, the same procedures were carried out as in Example 25 except that {3-acetoxymethyl-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (211 mg, 0.39 mmol) was employed as the starting material to obtain {3-(4'-pentenyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (149 mg, Yield: 70%) as substantially colorless oily product. This product also contained about 10% of a substance formed by a reaction of γ-attack.

IR (neat): 1645 cm$^{-1}$.

NMR δ (CDCl$_3$): 5.40-6.05 (m, 1H), 5.35 (m, 2H), 5.20 (bs, about 1H), 4.90 (m, 2H), 4.00 (m, 1H), 3.60 (m, 1H), 2.90 (m, about 1H).

Mass m/z: 487 (M$^+$-57).

EXAMPLE 32

In the method as described in Example 25, the same procedures were carried out as in Example 25 except that {3-acetoxymethyl-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (211 mg, 0.39 mmol) was employed as the starting material to obtain {3-(4'-pentenyl)-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (131 mg, Yield: 70%) as substantially colorless oily product. This product also contained about 10% of a substance formed by a reaction of γ-attack.

IR (neat): 1645 cm$^{-1}$.

NMR δ (CDCl$_3$): 5.40-6.05 (m, 1H), 5.35 (m, 2H), 5.20 (bs, about 1H), 4.90 (m, 2H), 4.55 (m, 2H), 4.00 (m, 1H), 3.40-3.70 (m, 5H), 2.90 (m, about 1H).

Mass m/z: 400 (M$^+$-84).

REFERENCE EXAMPLE 15

To a THF (1.2 ml) solution of {3-(4'-pentenyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (175 mg, 0.32 mmol) (Purity: about 90%) was added 9-BBN (0.42 mmol, 0.83 ml, 0.5M THF solution) at 0° C., and the mixture was stirred for 5 hours at the same conditions. After continuation of stirring at the room temperature for 0.5 hour, to the mixture were added a 6N NaOH aqueous solution (0.21 ml) and a 30% hydrogen peroxide aqueous solution (0.18 ml). After stirring at 60° C. for an hour, the mixture was diluted with water and extracted with ether. The separated ether layer was washed with a saturated aqueous sodium thiosulfate solution and a saturated saline solution and dried with anhydrous magnesium sulfate. After evaporation of the solvent, the residue was purified through silica gel column chromatography to obtain {3-(5'-hydroxypentyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (145 mg, Yield: 81%) as substantially colorless oily product.

IR (neat): 3350 cm$^{-1}$.

NMR δ (CDCl$_3$): 5.47 (m, 2H), 5.24 (m, 1H), 4.05 (m, 1H), 3.64 (m, 3H), 2.91 (m, 1H).

Mass m/z: 507 (M$^+$-57).

REFERENCE EXAMPLE 16

In the method as described in Reference example 15, the same procedures were carried out as in Reference example 15 except that {3-(4'-pentenyl)-6(S)-[3'(S)-tetrahydropyranyloxy-1'-trans-octenyl]-7(R)-tetrahydropyranyloxy-(1S,5S)-cis-bicyclo[3.3.0]oct-2-ene}(156 mg, 0.32 mmol) was employed as the starting material to obtain {3-(5'-hydroxypentyl)-6(S)-[3'(S)-tetrahydropyranyloxy-1'-trans-octenyl]-7(R)-tetrahydropyranyloxy-(1S,5S)-cis-bicyclo[3.3.0]oct-2-ene}

(121 mg, Yield: 75%) as substantially colorless oily product.

IR (neat): 3400 cm$^{-1}$.

NMR δ (CDCl$_3$): 5.45 (m, 2H), 5.24 (m, 1H), 4.60 (m, 2H), 4.05 (m, 1H), 3.40–3.70 (m, 7H), 2.91 (m, 1H).

Mass m/z: 420 (M+-84).

REFERENCE EXAMPLE 17

To {3-(5'-hydroxypentyl)-6(S)-[3'(S)-t-butyldimethylsilyloxy-1'-trans-octenyl]-7(R)-t-butyldimethylsilyloxy-(1S,5S)-cis-bicyclo[3.3.0]oct-2-ene} (22 mg, 0.039 mmol) was added a tetra-n-butylammonium fluoride solution (0.3 mmol, 0.3 ml, 1M THF solution), and the mixture was stirred at room temperature for 12 hours. The mixture was diluted with a saturated saline solution and then extracted with ethyl acetate. The separated organic layer was dried with anhydrous magnesium sulfate and the solvent was distilled out therefrom. The residue was separated and purified through silica gel column chromatography (ethyl acetate:acetone =95:5) to obtain {3-(5'-hydroxypentyl)-6(S)-[3'(S)-hydroxy-1'-trans-octenyl]-7(R)-hydroxy-(1S,5S)-cis-bicyclo[3.3.0]oct-2-ene} (13 mg, Yield: 100%) as substantially colorless viscous liquid.

IR (neat): 3350 cm$^{-1}$.

NMR δ (CDCl$_3$): 5.52 (m, 2H), 5.28 (bs, 1H), 4.07 (m, 1H), 3.65 (m, 3H), 2.97 (m, 1H).

Mass m/z: 318 (M+-18).

REFERENCE EXAMPLE 18

{3-(5'-hydroxypentyl)-6(S)-[3'(S)-tetrahydropyranyloxy-1'-trans-octenyl]-7(R)-tetrahydropyranyloxy-(1S,5S)-cis-bicyclo[3.3.0]oct-2-ene} (20 mg, 0.040 mmol) was dissolved in a mixed solvent (1 ml) of acetic acid-water-THF (3:1:1), and the mixture was heated at 60° C. for 3 hours. After the solvent was removed by distillation, to the residue was added small amount of a saturated aqueous sodium hydrogencarbonate solution and the mixture was extracted with ethyl acetate. The separated organic layer was dried with anhydrous magnesium sulfate. After evaporation of the solvent, the residue was purified through silica gel column chromatography to obtain {3-(5'-hydroxypentyl)-6(S)-[3'(S)-hydroxy-1'-trans-octenyl]-7(R)-hydroxy-(1S,5S)-cis-bicyclo[3.3.0]oct-2-ene} (13 mg, Yield: 100%) as substantially colorless viscous liquid. Each of the spectrum data thereof are completely agreed with those of the sample obtained in Reference example 17.

REFERENCE EXAMPLE 19

{3-(5'-Hydroxypentyl)-6(S)-[3'(S)-hydroxy-1'-trans-octenyl]- 7(R)-hydroxy-(1S,5S)-cis-bicyclo[3.3.0]oct-2-ene} (12 mg, 0.036 mmol) was dissolved in a mixed solvent of acetone-H$_2$O (1:4, 1.5 ml), and to the solution were added Pt, as a catalyst, which was obtained by reducing PtO$_2$ and sodium hydrogencarbonate (3.2 mg, 0.038 mmol), and the mixture was stirred at 60° C. for 24 hours under oxygen gas stream. After the catalyst was removed by filtration and the mixture was neutralized with a 10% HCl aqueous solution, acetone was removed by distillation. The residue was made acidic solution again with the addition of a 10% HCl aqueous solution, the mixture was sufficiently extracted with ethyl acetate. The extract was dried with anhydrous magnesium sulfate and distilled out the solvent to obtain (+)-9(0)-methano-Δ$^{6(9α)}$-PGI$_1$ (8 mg, Yield: 61%) as substantially colorless viscous oily product.

IR (neat): 3350, 1700, 1450, 1250 cm$^{-1}$.

NMR δ (CDCl$_3$): 5.60 (m, 2H), 5.31 (bs, 1H), 4.11 (m, 1H), 3.80 (m, 1H), 3.00 (m, 1H), 0.90 (t, J=6 Hz, 3H).

Mass (CI, NH$_3$) m/z: 368 (M+ +NH$_4$).

$[α]_D^{20}$ = +16° (c=0.25, MeOH).

REFERENCE EXAMPLE 20

In the method as described in Reference example 15, the same procedures were carried out as in Reference example 15 except that {3-(4'-pentenyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (173 mg, 0.32 mmol) was employed as the starting material to obtain {3-(5'-hydroxypentyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (140 mg, Yield: 80%) as substantially colorless oily product.

IR (neat): 3350 cm$^{-1}$.

NMR δ (CDCl$_3$): 5.47 (m, 2H), 5.24 (m, 1H), 4.05 (m, 1H), 3.64 (m, 3H), 2.91 (m, 1H).

Mass m/z: 505 (M+-57).

REFERENCE EXAMPLE 21

In the method as described in Reference example 16, the same procedures were carried out as in Reference example 16 except that {3-(4'-pentenyl)-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (154 mg, 0.32 mmol) (purity: about 90%) was employed as the starting material to obtain {3-(5'-hydroxypentyl)-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (115 mg, Yield: 72%) as substantially colorless oily product.

IR (neat): 3400 cm$^{-1}$.

NMR δ (CDCl$_3$): 5.45 (m, 2H), 5.24 (m, 1H), 4.60 (m, 2H), 4.05 (m, 1H), 3.40–3.70 (m, 7H), 2.91 (m, 1H).

Mass m/z: 418 (M+-84).

REFERENCE EXAMPLE 22

In the method as described in Reference example 17, the same procedures were carried out as in Reference example 17 except that {3-(5'-hydroxypentyl)-6(S)-[3'(S)-t-butyldimethylsilyloxy-3'-cyclopentyl-1'-trans-propenyl]-7(R)-t-butyldimethylsilyloxy-(1S,5S)-cis-bicyclo[3.3.0]oct-2-ene} (21 mg, 0.039 mmol) was employed as the starting material to obtain {3-(5'-hydroxypentyl)-6(S)-[3'(S)-hydroxy-3'-cyclopentyl-1'-trans-propenyl]-7(R)-hydroxy-(1S,5S)-cis-bicyclo[3.3.0]oct-2-ene} (12 mg, Yield: 100%) as substantially colorless viscous liquid.

IR (neat): 3350 cm$^{-1}$.

NMR δ (CDCl$_3$): 5.52 (m, 2H), 5.28 (bs, 1H), 4.07 (m, 1H), 3.65 (m, 3H), 2.97 (m, 1H).

Mass m/z: 316 (M+-18).

REFERENCE EXAMPLE 23

In the method as described in Reference example 18, the same procedures were carried out as in Reference example 18 except that {3-(5'-hydroxypentyl)-6(S)-[3'(S)-tetrahydropyranyloxy-3'-cyclopentyl-1'-trans-propenyl]-7(R)-tetrahydropyranyloxy-(1S,5S)-cis-bicyclo[3.3.0]oct-2-ene} (19 mg, 0.040 mmol) was employed as the starting material to obtain {3-(5'-hydroxypentyl)-

6(S)-[3'(S)-hydroxy-3'-cyclopentyl-1'-trans-propenyl]-7(R)-hydroxy-(1S,5S)-cis-bicyclo[3.3.0]oct-2-ene} (12 mg, Yield: 100%) as substantially colorless viscous liquid. Each of the spectrum data thereof are completely agreed with those of the sample obtained in Reference example 22.

REFERENCE EXAMPLE 24

In the method as described in Reference example 19, the same procedures were carried out as in Reference example 19 except that {3-(5'-hydroxypentyl)-6(S)-[3'(S)-hydroxy-3'-cyclopentyl-1'-trans-propenyl]-7(R)-hydroxy-(1S,5S)-cis-bicyclo[3.3.0]oct-2-ene} (11 mg, 0.036 mmol) was employed as the starting material to obtain {3-(4'-carboxybutyl)-6(S)-[3'(S)-hydroxy-3'-cyclopentyl-1'-trans-propenyl]-7(R)-hydroxy-(1S,5S)-cis-bicyclo[3.3.0]oct-2-ene} (7 mg, Yield: 60%) as colorless white solid.

Melting point: 115° to 116° C. (recrystallized from ethyl acetate-n-hexane)

IR (neat): 3430, 2960, 1700, 1655 cm$^{-1}$.

NMR δ (CDCl$_3$): 5.62 (m, 2H), 5.32 (bs, 1H), 3.90 (m, 2H), 3.00 (m, 1H).

Mass (CI, NH$_3$) m/z: 366 (M$^+$ +NH$_4$).

TEST EXAMPLE 1

In the compounds synthesized by the method as described above, 9(0)-methano-Δ$^{6(9\alpha)}$-PGI$_1$, for example, has a biological activity as mentioned below. When the rabbit serum was employed, it depressd a cohesion of platelets to be induced by adenosine diphosphate (ADP) at a potency of 1/10 to that of PGI$_2$, and it showed a potency of ½ to that of PGI$_2$ when the human blood was employed. As for the effects to the blood pressure, when rat was examined, it showed the same effect as that of PGI$_2$ and showed blood pressure depressing action at a dosage of 0.1 μg/kg. An effect to the heart stroke frequencies thereof are almost the same as that of PGI$_2$, and increasing of the heart stroke frequencies were observed at a dosage of 1 μg/kg thereof in an experiment by using rats. As for an anti-fester action, it showed an activity at a low concentration of 10$^{-6}$M in an experiment by using rabbit stomach, and it was the same strength as that of PGE$_2$. Cytotoxicity thereof are extremely weak and IC$_{50}$=5 μg/ml.

TEST EXAMPLE 2

(+)-3-(4'-Carboxybutyl)-6(S)-[3'(S)-hydroxy-3'-cyclopentyl-1'-trans-propenyl]-7(R)-hydroxy-(1S,5S)-cis-bicyclo[3.3.0]oct-2-ene has biological activities as shown below. By using rabbit stomach epithelial cells, an experiment according to the method of Murota et. al. [K. Matsuoka, Y. Mitsui, and S. Murota, *J. Pharm. Dyn.*, 5, 991 (1982)] was carried out to obtain the result that it showed a remarkable anti-fester action at a low concentration of 0.5×10$^{-6}$M. This effect is the same as that of PGE$_2$ which is representative prostaglandin having anti-fester action. The above carbacyclin derivatives has no diarrhea inductive effect whereas the PGE$_2$ induces heavy diarrhea.

We claim:

1. A bicyclo[3.3.0]octene derivative represented by the formula:

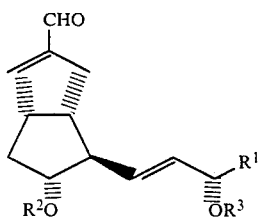

wherein
R$^1$ is a straight, branched or cyclic alkyl group or alkenyl group each having 5 to 10 carbon atoms; and
R$^2$ and R$^3$ are each separately a hydrogen atom or a protective group of a hydroxy group.

* * * * *